(12) United States Patent
Yan et al.

(10) Patent No.: US 11,596,296 B2
(45) Date of Patent: Mar. 7, 2023

(54) ENDOSCOPE

(71) Applicant: ANQING MEDICAL CO., LTD, Shanghai (CN)

(72) Inventors: Hang Yan, Shanghai (CN); Wei Tang, Shanghai (CN)

(73) Assignee: ANQING MEDICAL CO., LTD, Shanghai (CN)

( * ) Notice: Subject to any disclaimer, the term of this patent is extended or adjusted under 35 U.S.C. 154(b) by 298 days.

(21) Appl. No.: 16/649,987

(22) PCT Filed: Jan. 29, 2019

(86) PCT No.: PCT/CN2019/073617
§ 371 (c)(1),
(2) Date: Mar. 24, 2020

(87) PCT Pub. No.: WO2019/218726
PCT Pub. Date: Nov. 21, 2019

(65) Prior Publication Data
US 2020/0237188 A1 Jul. 30, 2020

(30) Foreign Application Priority Data

May 17, 2018 (CN) .......................... 201810476561.7
Nov. 2, 2018 (CN) .......................... 201811301672.0

(51) Int. Cl.
*A61B 1/00* (2006.01)
*A61B 1/005* (2006.01)

(52) U.S. Cl.
CPC .......... *A61B 1/0052* (2013.01); *A61B 1/0057* (2013.01); *A61B 1/00064* (2013.01); *A61B 1/00112* (2013.01)

(58) Field of Classification Search
CPC .............. A61B 1/0052; A61B 1/00064; A61B 1/00112; A61B 1/0057
See application file for complete search history.

(56) References Cited

U.S. PATENT DOCUMENTS 5,807,241 A * 9/1998 Heimberger ......... A61B 1/0055
600/142
2005/0272978 A1* 12/2005 Brunnen ................ A61B 1/008
600/142

(Continued)

FOREIGN PATENT DOCUMENTS

| CN | 1723835 A | 1/2006 |
|---|---|---|
| CN | 103764008 A | 4/2014 |

(Continued)

*Primary Examiner* — Anh Tuan T Nguyen
*Assistant Examiner* — Rynae E Boler
(74) *Attorney, Agent, or Firm* — Bayramoglu Law Offices LLC

(57) ABSTRACT

An endoscope includes an insertion portion provided with a controllable curved tube. The controllable curved tube includes a plurality of circular tube sections connected in series. A first C-shaped engaging portion is arranged at one end of each tube section. A first included angle is formed between the opening direction of the first C-shaped engaging portion and the axial direction of the tube section to which the first C-shaped engaging portion belongs. A first C-shaped notch is arranged around the outside of the first C-shaped engaging portion. The other end of the tube section is provided with a second C-shaped engaging portion that is engaged with the first C-shaped notch of another tube section. The inner side of the second C-shaped engaging portion is provided with a second C-shaped notch and a spherical protrusion which are engaged with a first C-shaped engaging portion of another tube section.

20 Claims, 3 Drawing Sheets

(56) References Cited

U.S. PATENT DOCUMENTS

2016/0345947 A1* 12/2016 Salahieh .......... A61B 17/00234
2020/0237189 A1*  7/2020 Do ........................ B23K 26/08

FOREIGN PATENT DOCUMENTS

| CN | 106659367 A   | 5/2017  |             |
|----|---------------|---------|-------------|
| CN | 107520273 A   | 12/2017 |             |
| CN | 108125665 A   | 6/2018  |             |
| CN | 108577789 A   | 9/2018  |             |
| CN | 108836235 A   | 11/2018 |             |
| EP | 2581031 A1 *  | 4/2013  | ........... A61B 1/0055 |
| EP | 2581031 A1    | 4/2013  |             |

* cited by examiner

ENDOSCOPE

CROSS REFERENCE TO THE RELATED APPLICATIONS

This application is the national phase entry of International Application No. PCT/CN2019/073617, filed on Jan. 29, 2019, which is based upon and claims priority to Chinese Patent Applications No. 201810476561.7, filed on May 17, 2018, and No. 201811301672.0, filed on Nov. 2, 2018, the entire contents of which are incorporated herein by reference.

TECHNICAL FIELD

The present disclosure relates to the field of medical instruments, and more particularly to an endoscope including a controllable curved tube.

BACKGROUND

Endoscopes used in industry or medical treatment are provided with an insertion portion to be inserted into a living body or a tube. Generally, for an endoscope having flexible insertion portion, there is a controllable curved portion arranged at the front end of the insertion portion. The curved portion can be bent as need by means of an operation device. Therefore, in an endoscope having curved portion, the direction of the observation portion arranged at the front end can be oriented to a desired direction by the operation device.

Patent CN 200510076111.1 discloses a bendable portion. The bendable portion is arranged at the distal end of the insertion tube of the endoscope and includes a plurality of tube sections, each of the plurality of tube sections is provided with a connecting device, and the connecting device cooperates with a connecting device of an adjacent tube section. The bendable portion further includes a control line, and the control line can control the bendable portion to bend. Each connecting device of the plurality of tube sections is arranged in a manner that each connecting device axially protrudes from the respective surfaces and is positioned in the housing of the tube section. The thickness of each connecting device is smaller than or equal to the thickness of the housing. The connecting devices, which are arranged on the respective surfaces of the adjacent tube sections and positioned opposite to one another, are complementary to one another in a hinge-type connection manner.

Patent CN 201280041664.1 discloses a curved portion. The curved portion includes a group of bending pieces in which a plurality of bending pieces are successively arranged in a freely rotatable manner. The bending piece group is composed of the plurality of bending pieces and engaging portions, wherein the plurality of bending pieces are formed by cutting a rigid tube, two sides of each bending piece are respectively provided with a convex portion and a concave portion where the engaging portion is arranged, and the plurality of bending pieces are rotatably connected by the engaging portions. The engaging portion includes a first engaging portion, and the first engaging portion includes a first convex portion formed on one side of the bending piece by cutting and a first concave portion that is formed on the other side of the bending piece and allows the first convex portion to slide therein. The engaging portion further includes a second engaging portion, and the second engaging portion is formed by a pair of second convex portions formed on the other side of the bending piece and separated from the first concave portion by cutting and a pair of second concave portions which are formed on one side of the bending piece and allow the pair of second convex portions to slide therein. The bending piece is provided with any one of a first reinforcing portion that cuts out a portion of the bottom of the first concave portion and widens the bending piece end on one end side and a second reinforcing portion that widens the bending piece end on the other end side from the bottom surface of the pair of second concave portions.

Patent CN201580047959.3 discloses an endoscope device provided with a curved tube having an enhanced resistance to an external force, the external force is applied to a plurality of bending pieces that are formed and connected by laser drawing, and the external force includes pulling, bending and twisting. In order to achieve the above objective, the curved tube according to an embodiment of the present disclosure includes: a first bending piece, configured to form a bendable curved tube; a second bending piece, configured to rotate relative to the first bending piece; a connecting rod, formed on the first bending piece and having a rotating shaft around which the second bending piece rotates; an engaging portion, formed on the second bending piece and having a sliding surface that is substantially parallel to the rotating shaft and slides relative to the connecting rod, wherein the engaging portion is rotatably engaged with the connecting rod; and a receiving portion, formed adjacent to the connecting rod in the first bending piece and having a vertical surface, wherein the vertical surface abuts the engaging portion when the engaging portion engaged with the connecting rod rotates and the vertical surface is formed in a direction substantially perpendicular to the rotating shaft.

However, in the above-mentioned curved tube structures disclosed in the prior art, the structures for connecting the bending pieces or tube sections that form the curved tube are notches and protrusions that are engaged with one another, the opening direction of the notch is consistent with the axial direction of the curved tube, and the protrusion is engaged with the notch along the axial direction of the curved tube to connect the bending pieces or tube sections in series. In such a design, the bending piece or the tube section is prone to disengagement, which poses a potential safety risk to the surgery and affects the service life of the instrument.

SUMMARY

The present invention discloses an endoscope. An insertion portion of the endoscope is provided with a controllable curved tube. The controllable curved tube includes a plurality of circular tube sections connected in series and a control device configured to control the controllable curved tube to bend. A first C-shaped engaging portion is arranged at one end of each tube section. A first included angle is formed between the opening direction of the first C-shaped engaging portion and the axial direction of the tube section to which the first C-shaped engaging portion belongs. A first C-shaped notch is arranged around the outside of the first C-shaped engaging portion. The other end of each tube section is provided with a second C-shaped engaging portion that is engaged with the first C-shaped notch of another tube section. The inner side of the second C-shaped engaging portion is provided with a second C-shaped notch and a spherical protrusion which are engaged with the first C-shaped engaging portion of another tube section, and the second C-shaped notch surrounds the spherical protrusion.

When two adjacent tube sections are connected in series, the spherical protrusion of the first tube section of the two adjacent tube sections is engaged inside the first C-shaped engaging portion of the second tube section of the two adjacent tube sections, so that the first C-shaped engaging portion of the second tube section is inserted into the second C-shaped notch of the first tube section, and the second C-shaped engaging portion of the first tube section is inserted into the first C-shaped notch of the second tube section.

After being engaged, the first C-shaped engaging portion of the second tube section can move inside the second C-shaped notch of the first tube section, and the second C-shaped engaging portion of the first tube section can move inside the first C-shaped notch of the second tube section.

Optionally, the first included angle ranges from 10° to 90°.

Optionally, a second included angle is formed between the opening direction of the second C-shaped engaging portion and the axial direction of the tube section to which the second C-shaped engaging portion belongs, and the second included angle ranges from 10° to 90°.

Optionally, one end of each tube section is circumferentially provided with two sets of first C-shaped engaging portions and first C-shaped notches opposite to each other. Correspondingly, the other end of each tube section is circumferentially and oppositely provided with two sets of second C-shaped engaging portions as well as second C-shaped notch and spherical protrusion that are engaged with the first C-shaped engaging portions. After being engaged, a gap is formed between any two adjacent tube sections, and the gap is arranged to separate the two first C-shaped engaging portions or the two second C-shaped engaging portions and extends along the circumferential direction of the tube section.

Optionally, one or more grooves are arranged on tube section walls located at the gap formed between adjacent tube sections, and the grooves extend in the circumferential direction of each tube section.

Optionally, the control device includes one or more traction wires. The traction wires pass through one end of the tube sections connected in series, and are fixedly connected to the outermost tube section located on the other end of the tube sections connected in series.

Optionally, the tube section is further provided with one or more fixing portions configured to fix the traction wires.

Optionally, the fixing portions are uniformly and circumferentially distributed on the tube section.

Optionally, the fixing portion is a circular tube fixedly connected on the inner wall of the tube section.

Optionally, the curvature of the controllable curved tube changes as the length of the tube section at the corresponding position changes.

Optionally, the controllable curved tube is formed by cutting a metal tubular material.

In the endoscope according to the present disclosure, since an included angle is formed between the opening direction of the C-shaped engaging portion of each tube section that forms the curved tube and the axial direction of the tube section to which the C-shaped engaging portion belongs, so that the engaged spherical protrusions remain securely engaged during the bending process, which makes the connection between the tube sections firm and secure. The C-shaped engaging portion can move in the C-shaped notch to provide a curved space required for the bending of the curved tube, which is thus conducive to controlling the curvature by controlling the movement of the C-shaped engaging portion, provides significant convenience for surgical operations, and thus has a degree of utility.

Furthermore, in an alternative solution of the present disclosure, an included angle is also formed between the opening direction of the C-shaped notch and the axial direction of the curved tube, which further increases the security of the connection.

In order to make the above-mentioned contents of the present disclosure more comprehensible, the preferred embodiments are described hereinafter in detail with reference to the drawings.

BRIEF DESCRIPTION OF THE DRAWINGS

The present disclosure will be described hereinafter with reference to the drawings.

DETAILED DESCRIPTION OF THE EMBODIMENTS

Figure 1:
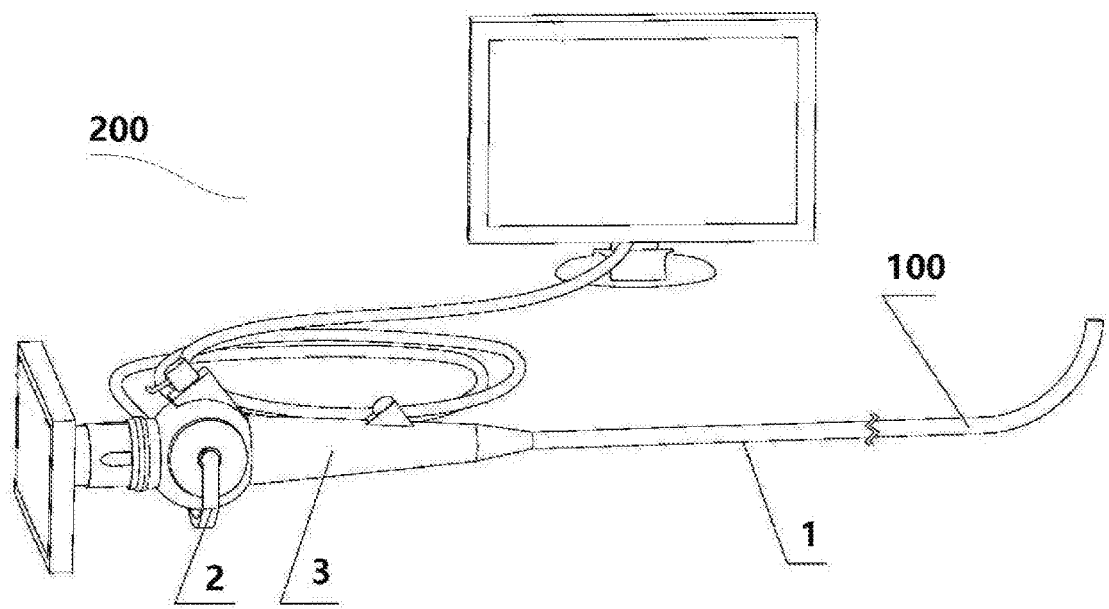
FIG. 1 is a schematic diagram showing the overall structure of the endoscope according to an embodiment of the present disclosure.

The implementation modes of the present disclosure will be described hereinafter with reference to the embodiments. Those skilled in the art can easily understand other advantages and functions of the present disclosure from the content disclosed in this specification.

The illustrative embodiments of the present disclosure will be described with reference to the drawings. However, the present disclosure may be implemented in many different forms and is not limited to the embodiments described herein. These embodiments are provided to expressly and completely disclose the present disclosure, and to fully convey the scope of the present disclosure to those skilled in the art. The terminologies in the illustrative embodiments and drawings are not construed as a limitation on the present disclosure. In the drawings, the same units/elements use the same reference numerals.

Unless otherwise stated, the terminologies (including scientific and technical terminologies) used herein have the ordinary definitions to those skilled in the art. In addition, it can be understood that the terminologies defined in commonly used dictionaries should be construed as the definitions consistent with the context of the related fields rather than the idealized definitions or overly formal definitions.

Figure 2:
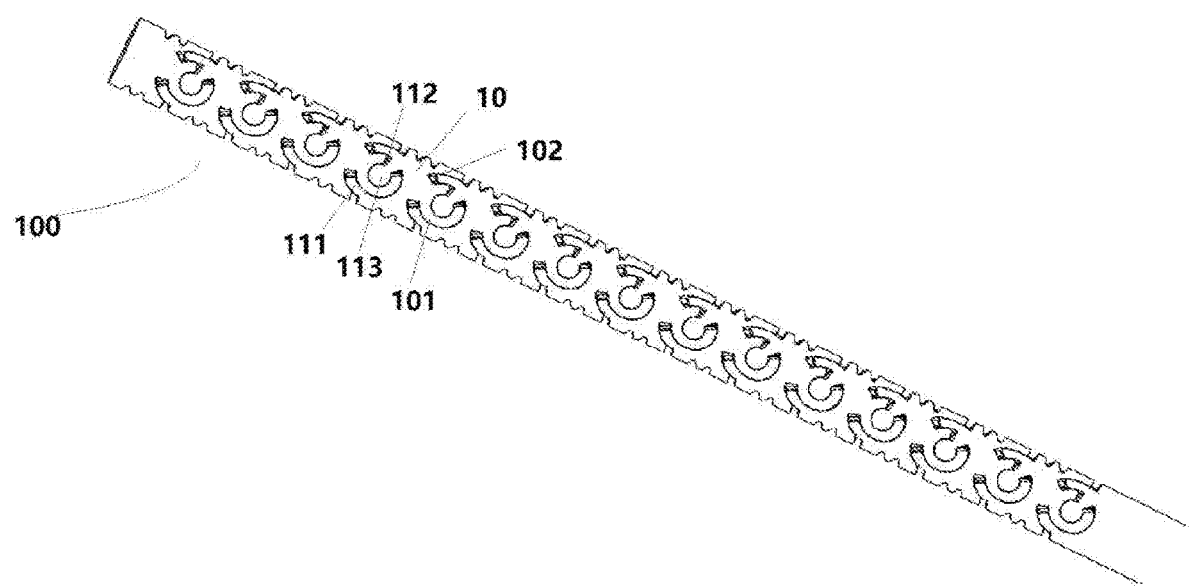
FIG. 2 is a side view of the controllable curved tube of the endoscope according to an embodiment of the present disclosure.

As shown in FIG. 1, an embodiment of the present disclosure provides the endoscope 200 to which the controllable curved tube mentioned above is applied. The controllable curved tube structure as described above is provided on the front end of the insertion portion of the endoscope inserted into a living body or a tube. As shown in FIG. 2, the endoscope may include: the insertion tube 1 for the endoscope, the control device 2, and the handle 3. A portion of the insertion tube 1 that can enter the human body is provided with the controllable curved tube 100.

The structure of the controllable curved tube 100 shown in FIG. 2 includes a plurality of circular tube sections 10 connected in series that form the controllable curved tube. As can be seen from FIG. 3, one end of each tube section 10 is provided with the first C-shaped engaging portion 101. The first included angle r is formed between the opening direction of the first C-shaped engaging portion and the axial direction of the tube section 10 to which the first C-shaped engaging portion belongs. The first C-shaped notch 102 is arranged around the outside of the first C-shaped engaging portion 101. The other end of the tube section 10 is provided with the second C-shaped engaging portion 111 that is engaged with the first C-shaped notch of another tube section 10. The inner side of the second C-shaped engaging portion 111 is provided with the second C-shaped notch 112 and the spherical protrusion 113 which are engaged with the first C-shaped engaging portion 101 of another tube section 10, and the second C-shaped notch 112 surrounds the spherical protrusion 113.

When the tube section 10 is connected in series with the adjacent tube section 10', the spherical protrusion 113 of the tube section 10' is engaged inside the first C-shaped engaging portion 101 of the tube section 10, so that the first C-shaped engaging portion 101 of the tube section 10 is inserted into the second C-shaped notch 112 of the tube section 10', and the second C-shaped engaging portion 111 of the tube section 10' is inserted into the first C-shaped notch 102 of the tube section 10. After being engaged, the first C-shaped engaging portion 101 of the tube section 10 and the second C-shaped engaging portion 111 of the tube section 10' can move inside the second C-shaped notch 112 of the tube section 10' and the first C-shaped notch 102 of the tube section 10, respectively.

If the tube section and an adjacent tube section thereof are respectively denoted as a first tube section and a second tube section, then, the forgoing description can also be applied as follow: When two adjacent tube sections are connected in series, the spherical protrusion 113 of the first tube section is engaged inside the first C-shaped engaging portion 101 of the second tube section, so that the first C-shaped engaging portion 101 of the second tube section is inserted into the second C-shaped notch 112 of the first tube section, and the second C-shaped engaging portion 111 of the first tube section is inserted into the first C-shaped notch 102 of the second tube section.

After being engaged, the first C-shaped engaging portion 101 of the second tube section can move inside the second C-shaped notch 112 of the first tube section, and the second C-shaped engaging portion 111 of the first tube section can move inside the first C-shaped notch 102 of the second tube section.

Specifically, if these tube sections need to be connected together and pivoted without applying additional devices such as bolts, a clamping structure needs to be arranged at one end of the tube section to clamp or engage the protruding portion of the other end of the adjacent tube section. In the embodiment of the present disclosure, the first C-shaped engaging portion 101 is provided at the tube section, the second C-shaped notch 112 that is engaged with the first C-shaped engaging portion is arranged at the adjacent tube section, and the spherical protrusion 113 is provided on a side of the center of the second C-shaped notch. Since the first included angle r is formed between the opening direction of the second C-shaped engaging portion 112 and the axial direction of the tube section to which the second C-shaped engaging portion 112 belongs, the spherical protrusion 113 needs to be provided on the side of the center of the second C-shaped notch 112 in accordance with the opening direction, and is offset to the axial direction of the tube section. The diameter of the spherical protrusion 113 is larger than the diameter of the opening of the first C-shaped engaging portion 101, so that the spherical protrusion 113 is offset to the axial direction and is engaged at the center of the first C-shaped engaging portion 101. It is specifically understood as follows. The spherical protrusion includes a spherical portion and a connecting portion, and the connecting portion is connected to the second C-shaped engaging portion 111 and the spherical portion, respectively. The spherical protrusion 113 described above is offset in the axial direction, which can be understood that the connecting portion is offset in the axial direction. Namely, an included angle is formed between the direction connecting the spherical portion and the second C-shaped engaging portion 111 and the axial direction. The spherical protrusion described above is engaged in the center of the first C-shaped engaging portion 101, which can be understood that the spherical portion is engaged in the center of the first C-shaped engaging portion 101.

In this way, whether extended or bent, the spherical protrusion 113 is difficult to disengage from the opening of the first C-shaped engaging portion 101 and can be securely engaged in the first C-shaped engaging portion 101, and the first C-shaped engaging portion 101 can move in the second C-shaped notch 112 to provide a bending space for the tube body, so as to ensure the controllability of bending, and also improves the stability of the connection between the tube sections.

The tube section 10 in the embodiments of the present disclosure has a simple structure and can be formed by laser cutting, which has a low processing cost and a high yield. The material of the tube wall is preferably a metal material, e.g. sus 304 (i.e. American Society for Testing Material (ASTM), America Iron and Steel Institute (AISI) 304), sus 316, or a nickel-titanium alloy. Non-metallic materials such as nylon, polyurethane (PU), thermoplastic polyurethane (TPU) elastomer rubber, polyvinyl chloride (PVC), thermoplastic elastomer (TPE) and other plastic materials can also be selected.

In one embodiment, the controllable curved tube is formed by cutting a metal tubular material. Namely, a plurality of tube sections connected in series may be formed by cutting the identical metal tubular material, which has a low cost and facilitates assembling.

In addition, in the embodiments of the present disclosure, the tube sections may be cut and formed separately, and then assembled.

In an alternative embodiment of the present disclosure, the first included angle r formed between the opening direction of the first C-shaped engaging portion 101 and the axial direction of the tube section 10 to which the first C-shaped engaging portion 101 belongs is in the range of 10° to 90°, and the first included angle within this range can achieve an optimal engaging and limiting effect, which not only facilitates the connection process, but also achieves a stable limiting effect, and thus can be well applied in practice.

According to an embodiment of the present disclosure, the first C-shaped notch 102 is arranged around the outside of the first C-shaped engaging portion 101. The other end of the tube section 10 is provided with the second C-shaped engaging portion 111 that is engaged with the first C-shaped notch 102 of another tube section 10. When the spherical protrusion 113 is engaged inside the first C-shaped engaging portion 101, the first C-shaped engaging portion 101 is inserted in the second C-shaped notch 112, and the second C-shaped engaging portion 111 is inserted in the first C-shaped notch 102. The second C-shaped engaging portion 111 also has an opening, and the direction of the opening may be the same as the axial direction of the tube section to which the second C-shaped engaging portion 111 belongs. Preferably, the direction of the opening and the axial direction of the tube section to which the second C-shaped engaging portion belongs can also form an included angle, i.e., the second included angle y shown in FIG. 3. When the tube body is extended or bent, the second C-shaped engaging portion 111 is difficult to disengage from the opening of the first C-shaped notch 102. This design provides a double limit protection, which can further increase the stability of the connection between the tube sections 10 and minimize the risk that the tube sections will disengage, and has a good application value.

Further, the second angle y formed between the opening direction of the second C-shaped engaging portion 111 and the axial direction of the tube section to which the second C-shaped engaging portion 111 belongs is in the range of 10° to 90°, and the second angle within this range can achieve an optimal engaging and limiting effect, which not only facilitates the connection process, but also achieves a stable limiting effect.

In an alternative solution of the embodiments of the present disclosure, the curvature of the controllable curved tube changes as the length of the tube section at the corresponding position changes. The curvature can be construed as the bending ability of the tube, and can also be understood that the higher the bending degree of controllable curved tube, the stronger the bending ability, and the greater the curvature.

Since the bending is caused by a relative rotation between the tube sections, and the maximum angle of the relative rotation between the two tube sections is determined. Therefore, if a line formed by the longer tube sections connected in series is regarded as an arc, the curvature radius of the arc is greater than the curvature radius of the arc generated when the shorter tube sections are connected in series. It can be seen that the bending degree is small, i.e., the curvature is small.

Figure 7:
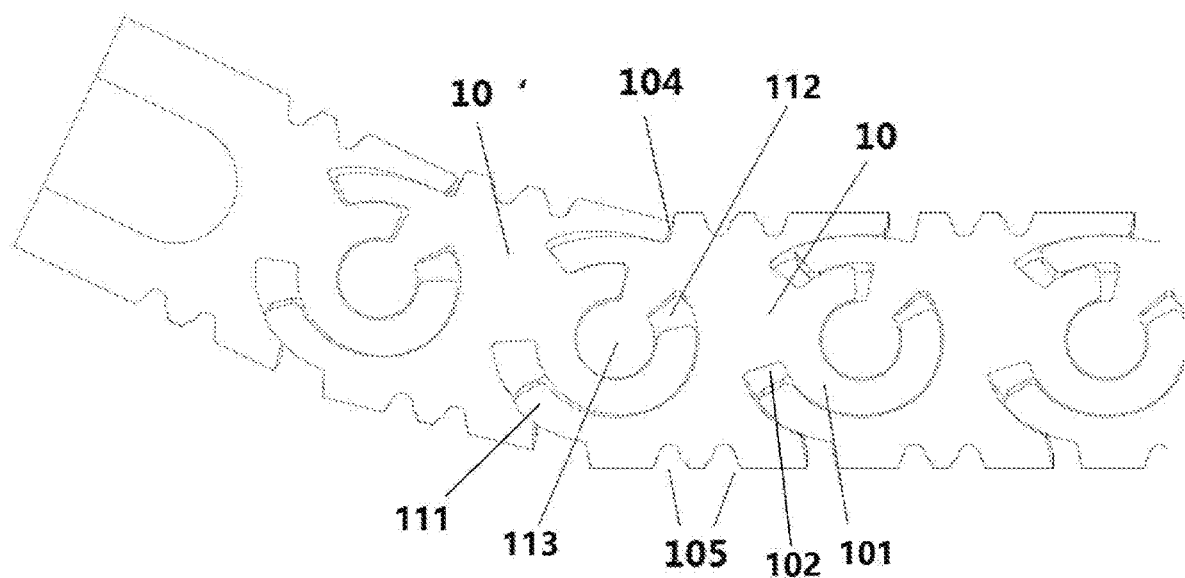
FIG. 7 is a schematic diagram showing a partially enlarged view of the bending state of the controllable curved tube of the endoscope according to an embodiment of the present disclosure.

In the embodiments of the present disclosure, one end of each tube section 10 may be circumferentially provided with multiple sets of first C-shaped engaging portions 101 and first C-shaped notches to satisfy the requirements for the bending direction in different application scenarios. In another preferred embodiment of the present disclosure, as shown in FIGS. 4 to 7, one end of each tube section 10 is circumferentially provided with two sets of first C-shaped engaging portions 101 and first C-shaped notches 102 opposite to each other. Correspondingly, the other end of each tube section 10 is circumferentially and oppositely provided with two sets of second C-shaped engaging portions 111 as well as second C-shaped notch 112 and spherical protrusion 113 that are engaged with the first C-shaped engaging portions 101. After being engaged, the gap 104 is formed between the adjacent tube sections 10, and the gap 104 is arranged to separate the C-shaped engaging portions and extends along the circumferential direction of the tube section. The controllable curved tube of the present embodiment can be bent in two directions controlled by the control device. The gap 104 provides a bending space for the bending of the controllable curved tube 100. As shown in FIG. 7, when the controllable curved tube undergoes a bending deformation in one direction, the first C-shaped engaging portion 101 of each tube section 10 moves in the second C-shaped notch 112 of the adjacent tube section 10'. Specifically, the first C-shaped engaging portion 101 rotates around the spherical protrusion 113 by a certain angle, and the opening direction of the second C-shaped notch 112 changes accordingly. The gap 104, provided between the first C-shaped engaging portions 101, increases at one side and decreases at the other side to provide the space required for the bending of the tube body. When the controllable curved tube is bent to the other side, all the above changes are generated in reverse. In this way, the controllable curved tube 100 in the present embodiment can be bent in two directions. Those skilled in the art should understand that the first C-shaped engaging portion should not be limited by the positions and numbers provided in the present embodiment, and can be correspondingly designed according to specific application scenarios to meet different requirements for the bending direction.

Figure 5:
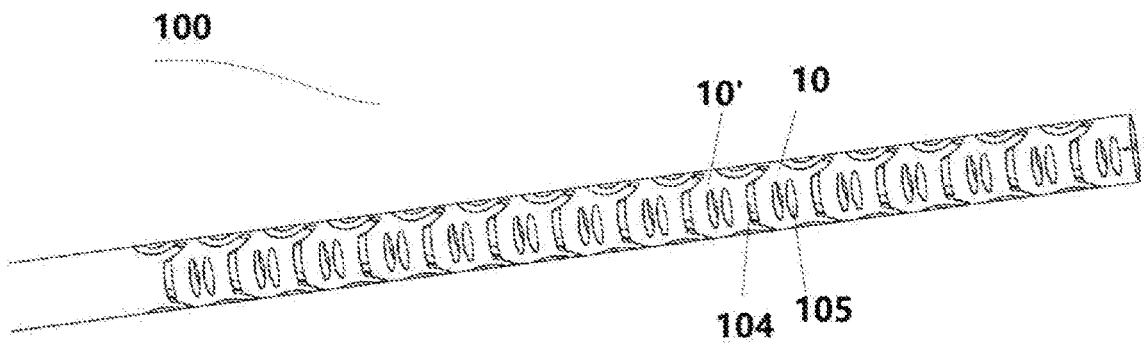
FIG. 5 is a schematic diagram showing another overall structure of the controllable curved tube of the endoscope according to an embodiment of the present disclosure.
Figure 6:
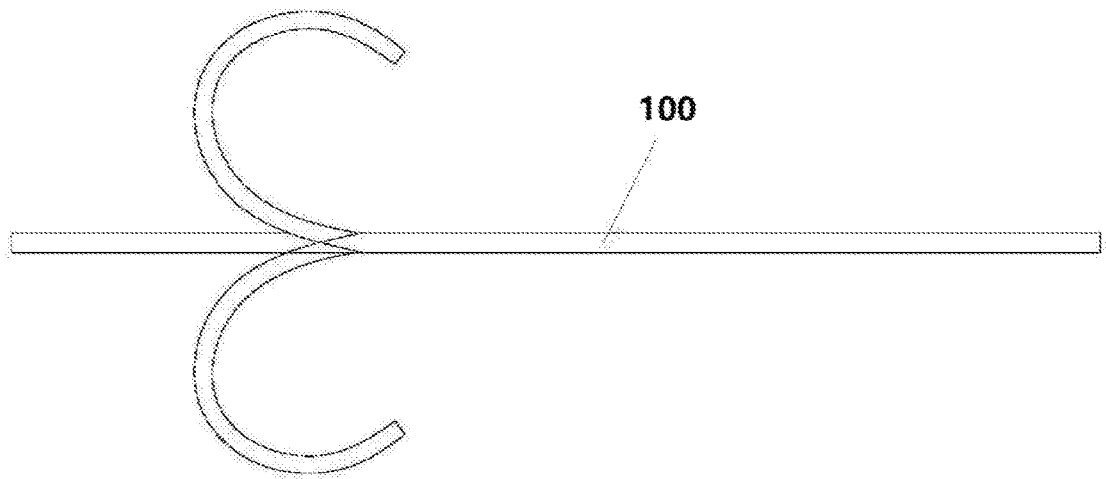
FIG. 6 is a schematic diagram showing an overall bending state of the controllable curved tube of the endoscope according to an embodiment of the present disclosure.

As can be seen from FIG. 5, one or more grooves 105 may be provided between the gaps 104 formed by each tube section 10 and the adjacent tube section 10'. The groove 105 extends in the circumferential direction of the tube section 10, and the groove 105 comes in various shapes such as a circle, a square, or a strip. As shown in FIG. 5, two elongated grooves 105 parallel to each other are arranged between the gaps 104 of each tube section 10. The groove 105 can further provide the space required for the bending of the tube body, increase the range of bending angle of the controllable curved tube, and enhance the flexibility of the tube body, reduce the weight and manufacturing cost of the tube body.

In order to enable the user to better control the controllable bending device, in an embodiment of the present disclosure, the control device is further configured to control the tube sections 10 connected in series. Further, the control device is preferably one or more traction wires configured to control the tube sections 10 connected in series to bend in one or more directions. The traction wire penetrates from one end of the tube sections 10 connected in series and is fixedly connected to the outermost tube section 10 located at the other end of the tube sections 10 connected in series. When an external force is applied to the traction wire, i.e., the traction wire is pulled to drive the tube section 10 fixedly connected to the traction wire to move. At this point, the first C-shaped engaging portion 101 on the tube section 10 rotates relative to the spherical protrusion 113 of the adjacent tube section 10'. When the C-shaped engaging portion 101 of the tube section 10 rotates to the extreme position of the second C-shaped notch 112 of the adjacent tube section 10', the traction wire continues to be pulled to drive the adjacent tube section 10' to continue to rotate, so that the entire bending device is bent. After the bending device is bent to the angle required by the user, the external force applied to the bending device is removed and the traction wire is fixed, so that the bending device can be maintained in the bent position.

Further, in an embodiment of the present disclosure, the traction portion preferably comprises a steel wire, but is not limited to the above. The traction portion can also be any filamentous structure, and the filamentous structure can also be made of any metal or non-metallic material.

In order to allow the traction wire to be well matched with the bending device and prevent the traction wire from moving in the tube section 10 of the bending device which affects the bending effect, in an embodiment of the present disclosure, the tube section 10 can be further provided with one or more fixing portions configured to fix the traction wires. In an embodiment of the present disclosure, preferably, one or two traction wires may be arranged in the plurality of tube sections 10 connected in series to function as the control device 20, so that the controllable bending device can be bent in one or two directions. Further, in the present embodiment, when a plurality of fixing portions are arranged on the tube section 10, the plurality of fixing portions are uniformly distributed on the tube section 10 to ensure that the bending device can be bent in all directions.

Further, the fixing portion may be a circular tube fixedly connected on the inner wall of the tube section 10, or may be a wire groove formed on the inner wall of the tube section 10. The traction wire is fixed by the fixing portion to prevent the traction wire from slipping off to avoid a failure of the controllable bending device. In the present disclosure, the controllable bending device can use the control portion to bend the tube section group according to the needs of the user, and the tube section can be bent in any direction required by the user, which is flexible and convenient. The foregoing is a preferred control method for controlling the controllable curved tube, those skilled in the art can know that, in practice, many control methods or control devices for controlling the controllable curved tube to bend in a desired direction are also available, and are not limited to the control device provided in the foregoing preferred embodiment.

In an embodiment of the present disclosure, the insertion end of the insertion tube 1 is further provided with a camera and one or more light sources, and the camera is connected to a monitor. The non-inserted end of the insertion tube 1 is provided with the handle 3, and the control device 2 for controlling the bending of the controllable bending device can be arranged on the handle 3. When the camera is shooting, the light source provides a bright shooting environment for the camera, and the monitor displays an image captured and output by the camera. When the insertion tube 1 enters the human body, the camera can also shoot the process of entering the human body, transmit and display the captured frames on the monitor. After the insertion tube 1 reaches a predetermined position in the human body, the camera can shoot the environment in the human body, and meanwhile the captured real-time frames are displayed on the monitor for the user to observe.

Figure 3:
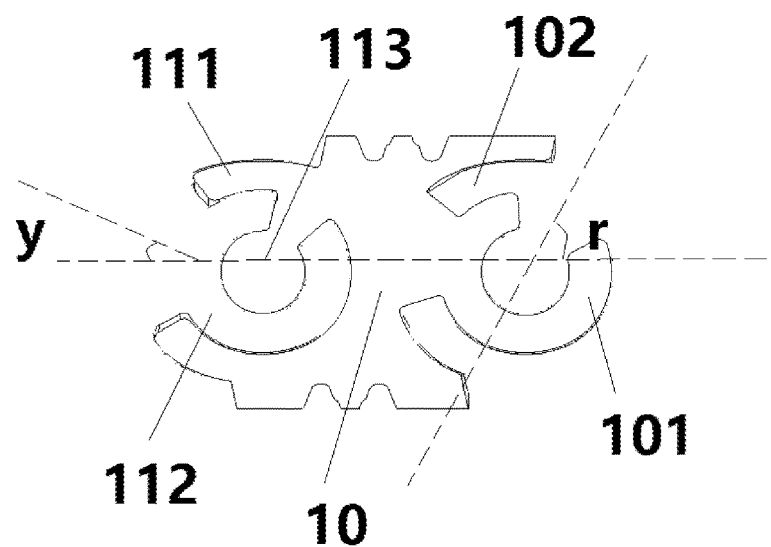
FIG. 3 is a structural schematic diagram of the tube section according to an embodiment of the present disclosure.
Figure 4:
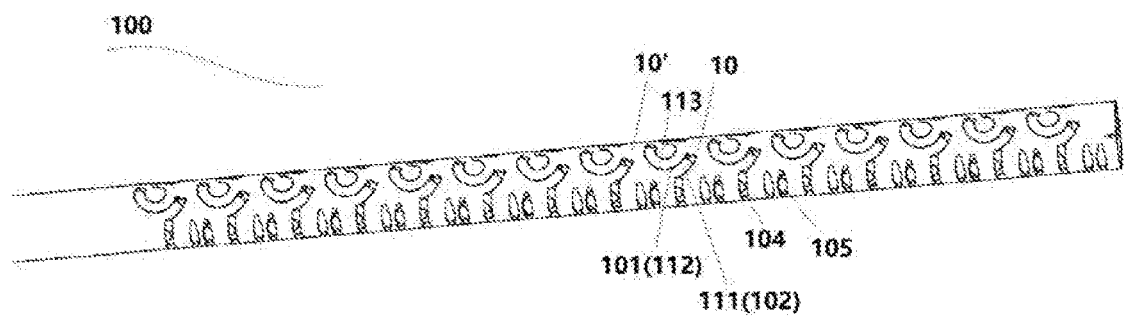
FIG. 4 is a schematic diagram showing the overall structure of the controllable curved tube of the endoscope according to an embodiment of the present disclosure.

In the above-mentioned embodiment, the controllable curved tube 100 arranged on the insertion tube 1 includes a plurality of circular tube sections 10 connected in series to form the controllable curved tube. As shown in FIG. 3, one end of each tube section 10 is provided with the first C-shaped engaging portion 101. The first included angle r is formed between the opening direction of the first C-shaped engaging portion and the axial direction of the controllable curved tube. The first C-shaped notch 102 is arranged around the outside of the first C-shaped engaging portion 101. The other end of the tube section 10 is provided with the second C-shaped engaging portion 111 that is engaged with the first C-shaped notch. The inner side of the second C-shaped engaging portion 111 is provided with the second C-shaped notch 112 and the spherical protrusion 113 which are engaged with the first C-shaped engaging portion 101, and the second C-shaped notch 112 surrounds the spherical protrusion 113. When the tube section 10 is connected in series with the adjacent tube section 10', the spherical protrusion 113 is engaged inside the first C-shaped engaging portion 101, so that the first C-shaped engaging portion 101 is inserted into the second C-shaped notch 112, and the second C-shaped engaging portion 111 is inserted into the first C-shaped notch 102. After being engaged, the first C-shaped engaging portion 101 and the second C-shaped engaging portion 111 can move inside the second C-shaped notch 112 of the adjacent tube section and the first C-shaped notch 102, respectively.

In the present embodiment, in order to provide a more comfortable feel for the operator, the handle 3 can also be arranged at the non-inserted end of the insertion tube 1 to facilitate the operation of the user. In order to make the connection between the handle 3 and the insertion tube 1 more reliable, a connecting member can also be arranged between the handle and the insertion tube to strengthen the connection between the handle and the insertion tube. Further, the handle 3 may be provided with the control device 2 for controlling the traction wire, and the control portion is connected to the traction wire to pull the traction wire, so as to realize the traction of the bending device to allow the bending device to bend.

In summary, in the controllable curved tube structure of the endoscope of the present disclosure, since an included angle is formed between the opening direction of the first C-shaped engaging portion of each tube section that forms the curved tube and the axial direction of the tube section to which the first C-shaped engaging portion belongs, during the bending, the engaged spherical protrusions remain securely engaged, so that the connections between the tube sections are more secure. The first C-shaped engaging portion can move inside the second C-shaped notch to generate a displacement, and the second C-shaped engaging portion can move inside the first C-shaped notch to generate a displacement, which provides the bending space required for the bending of the tube body, is advantageous to control the degree of bending by controlling the displacement, facilitates the surgical operation, and has a high practical value.

In addition, the foregoing embodiments of the present disclosure are only intended to illustrate the principle and advantages of the present disclosure rather than limiting the present disclosure. Those skilled in the art can make modifications or changes to the foregoing embodiments without departing from the spirit and scope of the present disclosure. Therefore, all equivalent modifications or changes made by those skilled in the art without departing from the spirit and technical concepts disclosed by the present disclosure shall still be covered by the claims of the present disclosure.

What is claimed is:

1. An endoscope, comprising:
a controllable curved tube;
wherein
an insertion portion of the endoscope is provided with the controllable curved tube;
the controllable curved tube comprises a plurality of circular tube sections connected in series and a control device configured to control the controllable curved tube to bend; a first C-shaped engaging portion is arranged at a first end of each circular tube section of the plurality of circular tube sections; wherein the first C-shaped engaging portion belongs to the first circular tube section; a first C-shaped notch is arranged around an outside of the first C-shaped engaging portion; a second end of each circular tube section is provided with a second C-shaped engaging portion, wherein the second C-shaped engaging portion is engaged with a first C-shaped notch of a second circular tube section of the plurality of circular tube sections; an inner side of the second C-shaped engaging portion is provided with a second C-shaped notch and a spherical protrusion, wherein the second C-shaped notch and the spherical protrusion are engaged with a first C-shaped engaging portion of the second circular tube section; and the second C-shaped notch surrounds the spherical protrusion;

when two adjacent circular tube sections of the plurality of circular tube sections are connected in series, a spherical protrusion of a third circular tube section of the two adjacent circular tube sections is engaged inside a first C-shaped engaging portion of a fourth circular tube section of the two adjacent tube sections, and the first C-shaped engaging portion of the fourth circular tube section is inserted into a second C-shaped notch of the third circular tube section, and a second C-shaped engaging portion of the third circular tube section is inserted into a first C-shaped notch of the fourth circular tube section;

after being engaged, the first C-shaped engaging portion of the fourth circular tube section moves inside the second C-shaped notch of the third circular tube section, and the second C-shaped engaging portion of the third circular tube section moves inside the first C-shaped notch of the fourth circular tube section, wherein a first included angle is formed between a center of an opening direction of the first C-shaped engaging portion and an axial direction of the first circular tube section, wherein the first C-shaped engaging portion belongs to the first circular tube section, and the first included angle ranges from 10° to 90°;

wherein the first end of each circular tube section is circumferentially provided with two sets of first C-shaped engaging portions and first C-shaped notches opposite to each other, the second end of each circular tube section is circumferentially and oppositely provided with two sets of second C-shaped engaging portions, second C-shaped notches and spherical protrusions, wherein the second C-shaped notches and the spherical protrusions are engaged with the two sets of first C-shaped engaging portions, after being engaged, a gap is formed between the two adjacent circular tube sections, and the gap is arranged to separate the two sets of first C-shaped engaging portions or the two sets of second C-shaped engaging portions; and the gap extends along a circumferential direction of each circular tube section; and wherein at least one groove is arranged on each tube section wall of each of the plurality of circular tube sections located near the gap formed between the two adjacent circular tube sections, the at least one groove extends in the circumferential direction of each circular tube section, and the at least one groove is not contiguous with the gap.

2. The endoscope according to claim 1, wherein, a second included angle is formed between a center of an opening direction of the second C-shaped engaging portion and the axial direction of the first circular tube section, wherein the second C-shaped engaging portion belongs to the first circular tube section, and the second included angle ranges from 10° to 90°.

3. The endoscope according to claim 1, wherein, the control device comprises at least one traction wire, and the at least one traction wire passes through a first end of the plurality of circular tube sections connected in series, and is fixedly connected to an outermost circular tube section located on a second end of the plurality of circular tube sections connected in series.

4. The endoscope according to claim 3, wherein, each circular tube section is further provided with at least one fixing portion configured to fix the at least one traction wire; and the at least one fixing portion is uniformly distributed in a circumferential direction of each circular tube section.

5. The endoscope according to claim 4, wherein, the at least one fixing portion is a circular tube fixedly connected on an inner wall of each circular tube section.

6. The endoscope according to claim 1, wherein, a curvature of the controllable curved tube changes as a length of each circular tube section at a position corresponding to the controllable curved tube changes.

7. The endoscope according to claim 1, wherein, the controllable curved tube is formed by cutting a metal tubular material.

8. The endoscope according to claim 1, wherein, the control device comprises at least one traction wire, and the at least one traction wire passes through a first end of the plurality of circular tube sections connected in series, and is fixedly connected to an outermost circular tube section located on a second end of the plurality of circular tube sections connected in series.

9. The endoscope according to claim 2, wherein, the control device comprises at least one traction wire, and the at least one traction wire passes through a first end of the plurality of circular tube sections connected in series, and is fixedly connected to an outermost circular tube section located on a second end of the plurality of circular tube sections connected in series.

10. The endoscope according to claim 1, wherein, a curvature of the controllable curved tube changes as a length of each circular tube section at a position corresponding to the controllable curved tube changes.

11. The endoscope according to claim 2, wherein, a curvature of the controllable curved tube changes as a length of each circular tube section at a position corresponding to the controllable curved tube changes.

12. The endoscope according to claim 1, wherein, the controllable curved tube is formed by cutting a metal tubular material.

13. The endoscope according to claim 2, wherein, the controllable curved tube is formed by cutting a metal tubular material.

14. An endoscope, comprising:
a controllable curved tube;
wherein
an insertion portion of the endoscope is provided with the controllable curved tube;
the controllable curved tube comprises a plurality of circular tube sections connected in series and a control device configured to control the controllable curved tube to bend; a first C-shaped engaging portion is arranged at a first end of each circular tube section of the plurality of circular tube sections; wherein the first C-shaped engaging portion belongs to the first circular tube section; a first C-shaped notch is arranged around an outside of the first C-shaped engaging portion; a second end of each circular tube section is provided with a second C-shaped engaging portion, wherein the second C-shaped engaging portion is engaged with a first C-shaped notch of a second circular tube section of the plurality of circular tube sections; an inner side of the second C-shaped engaging portion is provided with a second C-shaped notch and a spherical protrusion, wherein the second C-shaped notch and the spherical protrusion are engaged with a first C-shaped engaging portion of the second circular tube section; and the second C-shaped notch surrounds the spherical protrusion;

when two adjacent circular tube sections of the plurality of circular tube sections are connected in series, a spherical protrusion of a third circular tube section of the two adjacent circular tube sections is engaged inside a first C-shaped engaging portion of a fourth circular tube section of the two adjacent tube sections, and the first C-shaped engaging portion of the fourth circular tube section is inserted into a second C-shaped notch of the third circular tube section, and a second C-shaped engaging portion of the third circular tube section is inserted into a first C-shaped notch of the fourth circular tube section; and after being engaged, the first C-shaped engaging portion of the fourth circular tube section moves inside the second C-shaped notch of the third circular tube section, and the second C-shaped engaging portion of the third circular tube section moves inside the first C-shaped notch of the fourth circular tube section, wherein a second included angle is formed between a center of an opening direction of the second C-shaped engaging portion and the axial direction of the first circular tube section, wherein the second C-shaped engaging portion belongs to the first circular tube section, and the second included angle ranges from 10° to 90°;

wherein the first end of each circular tube section is circumferentially provided with two sets of first C-shaped engaging portions and first C-shaped notches opposite to each other, the second end of each circular tube section is circumferentially and oppositely provided with two sets of second C-shaped engaging portions, second C-shaped notches and spherical protrusions, wherein the second C-shaped notches and the spherical protrusions are engaged with the two sets of first C-shaped engaging portions, after being engaged, a gap is formed between the two adjacent circular tube sections, and the gap is arranged to separate the two sets of first C-shaped engaging portions or the two sets of second C-shaped engaging portions; and the gap extends along a circumferential direction of each circular tube section; and wherein at least one groove is arranged on each tube section wall of each of the plurality of circular tube sections located near the gap formed between the two adjacent circular tube sections, the at least one groove extends in the circumferential direction of each circular tube section, and the at least one groove is not contiguous with the gap.

15. An endoscope, comprising:
a controllable curved tube;
Wherein
an insertion portion of the endoscope is provided with the controllable curved tube;
the controllable curved tube comprises a plurality of circular tube sections connected in series and a control device configured to control the controllable curved tube to bend; a first C-shaped engaging portion is arranged at a first end of each circular tube section of the plurality of circular tube sections; wherein the first C-shaped engaging portion belongs to the first circular tube section; a first C-shaped notch is arranged around an outside of the first C-shaped engaging portion; a second end of each circular tube section is provided with a second C-shaped engaging portion, wherein the second C-shaped engaging portion is engaged with a first C-shaped notch of a second circular tube section of the plurality of circular tube sections; an inner side of the second C-shaped engaging portion is provided with a second C-shaped notch and a spherical protrusion, wherein the second C-shaped notch and the spherical protrusion are engaged with a first C-shaped engaging portion of the second circular tube section; and the second C-shaped notch surrounds the spherical protrusion;

when two adjacent circular tube sections of the plurality of circular tube sections are connected in series, a spherical protrusion of a third circular tube section of the two adjacent circular tube sections is engaged inside a first C-shaped engaging portion of a fourth circular tube section of the two adjacent tube sections, and the first C-shaped engaging portion of the fourth circular tube section is inserted into a second C-shaped notch of the third circular tube section, and a second C-shaped engaging portion of the third circular tube section is inserted into a first C-shaped notch of the fourth circular tube section; and after being engaged, the first C-shaped engaging portion of the fourth circular tube section moves inside the second C-shaped notch of the third circular tube section, and the second C-shaped engaging portion of the third circular tube section moves inside the first C-shaped notch of the fourth circular tube section, wherein a second included angle is formed between a center of an opening direction of the second C-shaped engaging portion and the axial direction of the first circular tube section;

wherein the first end of each circular tube section is circumferentially provided with two sets of first C-shaped engaging portions and first C-shaped notches opposite to each other, the second end of each circular tube section is circumferentially and oppositely provided with two sets of second C-shaped engaging portions, second C-shaped notches and spherical protrusions, wherein the second C-shaped notches and the spherical protrusions are engaged with the two sets of first C-shaped engaging portions, after being engaged, a gap is formed between the two adjacent circular tube sections, and the gap is arranged to separate the two sets of first C-shaped engaging portions or the two sets of second C-shaped engaging portions; and the gap extends along a circumferential direction of each circular tube section; and wherein at least one groove is arranged on each tube section wall of each of the plurality of circular tube sections located near the gap formed between the two adjacent circular tube sections, the at least one groove extends in the circumferential direction of each circular tube section, and the at least one groove is not contiguous with the gap.

16. The endoscope according to claim 1, further comprising an angle between the axial direction of the first circular tubular section and the second C-shaped engaging portion that is less than 90°.

17. The endoscope according to claim 14, wherein, the control device comprises at least one traction wire, and the at least one traction wire passes through a first end of the plurality of circular tube sections connected in series, and is fixedly connected to an outermost circular tube section located on a second end of the plurality of circular tube sections connected in series.

18. The endoscope according to claim 17, wherein, each circular tube section is further provided with at least one fixing portion configured to fix the at least one traction wire; and the at least one fixing portion is uniformly distributed in a circumferential direction of each circular tube section.

19. The endoscope according to claim 18, wherein, the at least one fixing portion is a circular tube fixedly connected on an inner wall of each circular tube section.

20. The endoscope according to claim 14, wherein, a curvature of the controllable curved tube changes as a length of each circular tube section at a position corresponding to the controllable curved tube changes.

* * * * *